(12) United States Patent
Klett et al.

(10) Patent No.: US 7,666,182 B2
(45) Date of Patent: Feb. 23, 2010

(54) HIGH-FREQUENCY SURGICAL APPARATUS AND A METHOD FOR OPERATING SAME

(75) Inventors: Johannes Klett, Ofterdingen (DE); Martin Heinrich, Hechingen (DE)

(73) Assignee: BOWA-electronic GmbH, Gomaringen (DE)

( * ) Notice: Subject to any disclaimer, the term of this patent is extended or adjusted under 35 U.S.C. 154(b) by 436 days.

(21) Appl. No.: 11/286,769

(22) Filed: Nov. 23, 2005

(65) Prior Publication Data

US 2006/0219682 A1    Oct. 5, 2006

(30) Foreign Application Priority Data

Nov. 23, 2004 (DE) ....................... 10 2004 056 636

(51) Int. Cl.
*A61B 18/12* (2006.01)
(52) U.S. Cl. .............................. 606/34; 606/39; 606/40
(58) Field of Classification Search .................. 606/34, 606/37–40, 45–52
See application file for complete search history.

(56) References Cited

U.S. PATENT DOCUMENTS

| | | | | |
|---|---|---|---|---|
| 4,500,837 A | * | 2/1985 | Shuey et al. ................. | 324/102 |
| 5,133,711 A | * | 7/1992 | Hagen .......................... | 606/38 |
| 5,423,810 A | * | 6/1995 | Goble et al. ................. | 606/40 |
| 5,849,010 A | * | 12/1998 | Wurzer et al. ................ | 606/39 |
| 5,976,128 A | * | 11/1999 | Schilling et al. ............. | 606/34 |
| 2004/0230189 A1 | * | 11/2004 | Keppel ......................... | 606/34 |

FOREIGN PATENT DOCUMENTS

| EP | 0 391 233 A2 | 10/1990 |
|---|---|---|
| EP | 0 709 065 A1 | 5/1996 |

* cited by examiner

*Primary Examiner*—Roy D Gibson
(74) *Attorney, Agent, or Firm*—Patent Central LLC; Stephen A. Pendorf

(57) ABSTRACT

The invention relates to a high-frequency surgical apparatus in which, for the purpose of cutting and/or coagulating biological tissue by means of high-frequency current, a high-frequency generator having a first electrode and a second electrode forms a high-frequency circuit through the tissue being treated, with an electric arc being formed, said apparatus having a measuring device to detect DC voltage components forming in the high frequency circuit when the arc is formed, said DC voltage components being usable for controlling the high-frequency generator via a controlling device. The invention is characterized in that the measuring device has an arc-decoupling circuit which separates the DC voltage components in the positive half-cycle of the high-frequency AC voltage from the DC voltage components in the negative half-cycle of the high-frequency AC voltage and makes available at least one of the separated DC voltage components as a signal for subsequent processing in the controlling device. The invention also relates to a corresponding method of running such apparatus.

12 Claims, 4 Drawing Sheets

HIGH-FREQUENCY SURGICAL APPARATUS AND A METHOD FOR OPERATING SAME

BACKGROUND OF THE INVENTION

1. Field of the Invention

The invention relates to a high-frequency surgical apparatus in which, for the purpose of cutting and/or coagulating biological tissue by means of high frequency current, a high-frequency generator having a first electrode and a second electrode creates a high frequency circuit through the tissue undergoing treatment, with an electric arc being formed, having a measuring device to detect DC voltage components generated in the high-frequency circuit when the arc is formed, which DC voltage components can be used to control the high-frequency generator via a controlling device.

2. Related Art of the Invention

The invention furthermore relates to a method for operating a high-frequency surgical apparatus in which, for the purpose of cutting and/or coagulating biological tissue by using high frequency current, a high-frequency generator having a first electrode and a second electrode creates a high frequency circuit through the tissue undergoing treatment, with an electric arc being formed, and in which the DC voltage components generated in the high frequency circuit when the electric arc is formed are used to control the high-frequency generator.

Apart from some specific coagulation effects (e.g. soft coagulation, desiccation), electrosurgical instruments for cutting or coagulating biological (e.g. human or animal) tissue function by making use of the photothermal and electrical properties of alternating electric arcs which ignite and extinguish between a first electrode and the organic tissue in contact with a second electrode, in step with the AC voltage half-waves generated by the HF generator. At the start of the application, the water-containing organic tissue in the contact zone is rapidly heated up and evaporated by the direct contact with the first electrode of the instrument. The cell membranes, which are approximately 8-10 nm thick, burst open in avalanche fashion as a result of the water vapour pressure at the site of the incision. The water vapour forms a thin, high-ohmic and dielectrical intermediate layer between the electrode and the organic tissue. If a sufficiently high voltage is applied, an electrical breakdown occurs with sparks or an electric arc being formed. In the process, the mixtures of water vapour and pyrolysis gas formed by combustion are ionized and water vapour molecules are thermally dissociated. The dynamics of the ionization and electric arcing result in specifically characteristic upper harmonics and shifts in potential (faradization) in the electric circuit, which can be used to control the HF generator.

A distinction is made between so-called monopolar operation and so-called bipolar (or more generally multipolar) operation. In the case of monopolar operation, the first electrode, which is usually referred to as the active electrode and is manipulated by the operator, has a relatively small surface area, while the second electrode, which is usually referred to as the neutral electrode, is applied to the patient over a large surface area. On the other hand, in the case of multipolar operation, several electrodes having comparable surface areas are provided, such as in the case of bipolar scissors or coagulation forceps.

The arc-induced action mechanisms discussed above, combined with HF power levels high enough to vapourize tissue, not only characterize the process of surgical cutting (electrotomy) using monopolar or bipolar techniques but they are also characteristic features in hemostasis (electrocoagulation), especially in the case of contactless monopolar spray coagulation and also in the case of contactless plasma coagulation carried out under argon protective gas (argon beamer).

One problem that occurs with all types of operation is the formation of an arc between two oppositely poled metals. It may happen, for example, that the operator accidentally causes a short circuit to occur between the first electrode and a further instrument being used or between the first electrode and a metallic implant. The resulting arc formation between the metal of the electrode and the metal of the other instrument or of the implant may result in a so-called metal burn being caused that can damage the electrode, instrument and/or implant. Also, especially in the case of endoscopic applications, vapourized metal may be deposited on optical elements, thereby gradually rendering them "blind".

DE 25 04 280 C3 discloses an HF generator control system that makes use of the upper harmonics in the current flow (harmonic component of the operating frequency of the HF oscillator), which are generated when the arc ignites and burns, as a measure of the magnitude or strength of the electric arc.

EP 0 709 065 A1 discloses an electrosurgical device in which voltage spikes introduced into the HF voltage by the formation of an electric arc are counted separately in the positive and the negative half wave of the HF voltage. This is achieved in two alternative fashions. In a first embodiment separate comparisons are performed between a threshold value and the peak amplitudes of the HF voltage on the one hand and between the same threshold value and the peak amplitudes of the inverted HF voltage on the other hand both yielding counts of voltage spikes in the positive and negative half waves respectively. In a second embodiment a high pass filter tuned to a frequency well above the HF frequency is used to allow only the very high frequency components of the voltage spikes to pass.

An alternative and less expensive means of controlling the HF generator is disclosed in DE 39 11 416 A1 as well as in the corresponding European patent application EP 0 391 233 A2. In the high-frequency surgical apparatus that is described there, which is designed for monopolar operation, control of the HF generator is based on detecting DC voltage components in the high-frequency circuit which occur as a result of asymmetrical discharge effects when the arc forms between the active electrode and the tissue in the HF circuit. The prior art high-frequency surgical apparatus has a DC voltage-measuring device designed as a discharge detection circuit, which device is connected to the electrical connections between the HF generator and the active electrode (instrument) and the neutral electrode which closes the HF circuit. The measuring device consists essentially of a current compensation choke on the output side of which a DC voltage, determined by the size of the arc, can be tapped off and then used to control the output power of the HF generator.

In the case of this prior art, generic method of controlling the electric arc, it is disadvantageous that when deviations from normal operation occur, especially when metal-to-metal arcing occurs, the controlling system fails, thereby resulting in undesirably high levels of power being applied to tissues or to the electrodes of the instruments, thus possibly harming the patients (necroses) or causing metal burn on implants and instruments.

SUMMARY OF THE INVENTION

It is the object of the present invention to improve the operating safety of the prior art high-frequency surgical instruments by DC voltage measurements to control the arc, and in particular to make it possible to detect undesired arcs between metals.

This object is achieved by providing the measuring device with an arc-decoupling circuit that separates the DC voltage components in the positive half-cycle of the HF alternating voltage from the DC voltage components in the negative half-cycle of the HF alternating voltage, and makes at least one of the separated DC voltage components available as a signal for subsequent processing in the controlling device.

The invention is based on the inventors' realization that the electron work functions of metals are similar, whereas the electron work function of biological tissue is significantly higher. This means that a very much lower voltage is needed in order to form an arc from the first electrode to the tissue than is required in the opposite direction. The arc that ignites whenever a threshold voltage dependent on the electron work function is exceeded can therefore occur much earlier in the one (positive) half wave of the HF voltage than in the other (negative) half wave. During normal operation, in which the arc burns between a first electrode and the tissue, and in which the HF voltage is reduced to the minimum level required for treatment purposes, the arc is therefore substantially unipolar, i.e. the spark jumps over only in the one (positive) half wave and always from the first electrode to the tissue.

An analysis of the voltage flow in the HF circuit has shown that in the case of a unipolar arc from the first electrode to the tissue, a first DC voltage component is observed in the one (positive) half wave of the AC voltage, whereas in the other (negative) half wave a significantly deviating second DC voltage component is determined. FIG. 4 shows a current-voltage hysteresis curve in the case of arc-based cutting of biological tissue.

When an electrode approaches metal, the ratio of the DC voltage components changes, or negative DC voltage components predominate (FIG. 5 shows a current-voltage hysteresis curve for the formation of an arc between a metal electrode and a metal placed on biological material). The reason for this is that the electron work functions of metals are similar, so that the formation of an arc from metal to metal can occur in both half waves of the HF voltage. The direction of the arc is thus stochastically distributed. The arc is no longer unipolar positive and the asymmetry of the unipolar operation is for the most part eliminated or greatly shifted.

The arc-decoupling circuit according to the invention now separates the DC voltage components of the positive and negative half waves. As provided for in a preferred embodiment of the invention, this can be accomplished by separately determining the DC voltage components of both half waves, i.e. of the positive as well as of the negative half wave, and by making appropriate signals available. However, it is in principle also possible to separate the half waves (and thus implicitly the DC voltage components which they contain) and to determine only the DC voltage component of one of the half waves, in particular the negative half wave, and then to make available an appropriate signal, if the subsequent processing requires just one of the DC voltage components.

The high frequency surgery apparatus according to the invention thus makes it possible to differentiate reliably the arcs forming between the following pairs of materials: biological tissue/metal and metal/metal. In this way, malfunctions or misapplications (short circuits between the electrode and the instrument, contact with implants, etc.) can be detected and measures can be initiated immediately to stop or prevent metal burn and undesired tissue damage. This improves the operating safety of the apparatus, provides increased safety for the patient and reduces the cost of HF-surgical applications.

According to a preferred embodiment of the invention, a measurement-processing device is provided down-stream from the arc-decoupling circuit, preferably in the form of a microcontroller, in which the signals filtered out of the HF voltage in the arc-decoupling circuit and separated according to DC voltage components from the positive half wave of the AC voltage and DC voltage components from the negative half wave of the AC voltage can be processed for preferably galvanically separated transmission of the signals to the subsequent controlling device.

The measurement-processing device has the advantage that a controlling device of conventional configuration can be used which, instead of the previous DC voltage signal, receives two DC voltage signals filtered and galvanically separated according to their origin. As a result, the arc-decoupling system according to the invention can be added relatively simply and cheaply to already existing arc-controlled electrosurgical instruments.

According to a further preferred embodiment of the invention, the controlling device has a computer unit with a processing algorithm and a data memory or a set point generator in which at least one set point input for at least one separated DC voltage component, or a value derived therefrom, can be stored or adjusted.

In the controlling device, effective voltage and current values for the HF generator are usually compared with set point inputs for these effective values and a desired voltage is adjusted or re-adjusted for the HF generator. According to the invention, the components from the negative and positive half waves are input separately as DC voltage values for control purposes. Correspondingly, special set point inputs may also be preset or can be adjusted for this purpose. For example, minimum and maximum limit values may be preset for DC voltage components from the positive and/or negative half wave, or limit values may be preset for the ratio of both, and measures to control the HF generator are initiated if said limit values are exceeded.

According to a further preferred embodiment of the invention, one measure may be to generate a control signal for controlling at least one of the parameters influencing the power output, taking into account the evaluation of the separated DC voltage signals. The actual controlling process might affect, for example, the current strength or the voltage, or it might also involve an emergency shutdown by interrupting an electrical connection. Thus, an automatic protective function can be integrated into the HF instrument via a control signal that takes into account the evaluation of the DC voltage components.

According to a further preferred embodiment of the invention, means to output a warning signal are assigned to the controlling device. The means for outputting the warning signal may take the form of a monitor with an optical and/or acoustic display. By means of an optical warning signal, for example a flashing signal on a display, and/or an acoustic warning signal, for example a specific warning sound, the operator is alerted to the fact that contact with metal, a short circuit or some other deviation from the regular arc exists. The operator can then immediately react by stopping the application or by changing the manipulation of the instrument so that harmful or undesired effects are avoided.

The prior art methods for operating a high-frequency surgical apparatus have the disadvantages described above.

A further task of the present invention is to improve prior art methods in such a way that the risk of the patient suffering undesired effects and also the risk of the surgical instruments being damaged while used for surgery is avoided or at least reduced.

This task is accomplished by measuring separately at least one of the positive and negative half-cycles of the high frequency AC voltage of the high frequency circuit to determine the occurrence of DC voltage components, and also by generating an appropriate signal if a DC voltage component deviates from a set point value setting. Preferably, both half-cycles are measured to determine the occurrence of DC voltage components.

With the help of these separate measurements, patients can be effectively protected from any unnecessary harmful effects on their health resulting from electrosurgical treatment. Measuring implies not only performing accurate measurement of the voltage values but also merely monitoring the AC voltage for the occurrence of undesired voltage components in the positive and/or negative half wave as a criterion for detecting contacts with implants and short circuiting of the instruments. This avoids unnecessary wear and tear on the surgical instruments used and the costs associated therewith, for example the frequent replacement of expensive filigree electrodes. This saves both costs and time and also ensures the long-term quality of the instruments.

According to a preferred embodiment of the invention, if at least one DC voltage component deviates from the set point value in the half-cycle of the high frequency AC voltage, an acoustic and/or an optical signal is emitted. In this way, if there is any deviation from the regular arc that is optimal for the application, the operator's work safety can be increased by giving him an appropriate signal, as he can thus immediately and appropriately react to feedback from the instrument.

According to a further preferred embodiment of the invention, if there is any deviation in the DC voltage component from the associated set point value in at least one half-cycle of the high frequency AC voltage, a control signal is generated via which the high frequency AC voltage is reduced or switched off. This type of automatic control by means of a control signal is capable of further enhancing operational safety in electrosurgery.

Further details regarding the invention can be obtained from the following detailed description and from the attached drawings, in which examples of preferred embodiments of the invention are depicted.

BRIEF DESCRIPTION OF THE DRAWINGS

The drawings show.

DETAILED DESCRIPTION OF THE INVENTION

A high-frequency surgical apparatus consists essentially of a high frequency generator 1, to which is attached an active electrode 5 and a neutral electrode 6, and also of an arc-measuring device 2 to control the HF generator 1.

Figure 1:
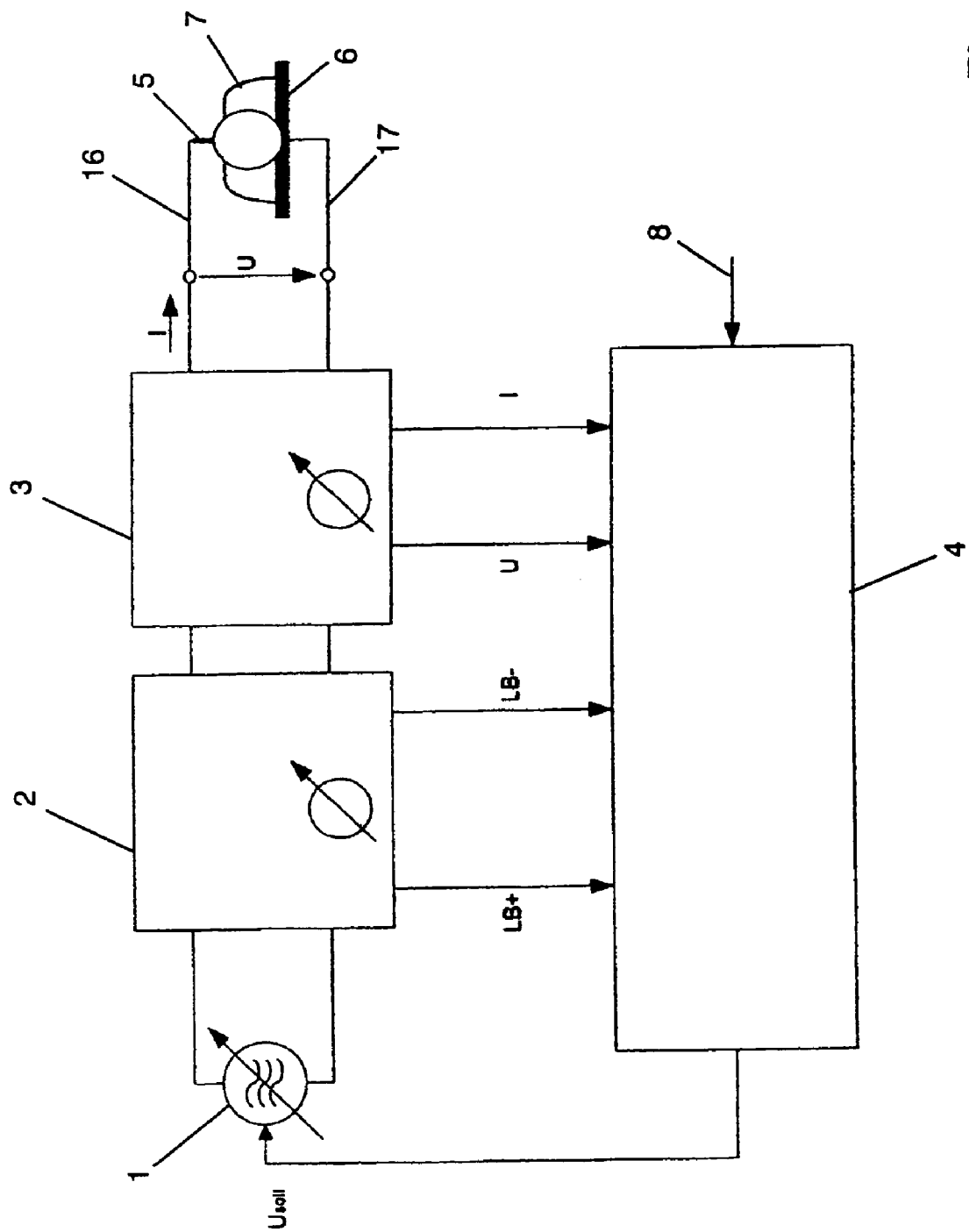
FIG. 1: A schematic circuit diagram of a high-frequency surgery device.

FIG. 1 shows a schematic circuit diagram of the high frequency surgical apparatus with a controllable power oscillator acting as the high frequency generator 1. The HF generator 1 is connected to the DC voltage side of a switching power supply unit, which is not shown here, and generates a high-frequency AC voltage of several hundred kHz. The active electrode 5 is connected to the HF generator 1 via a first electrical connection 16, and the neutral electrode 6 is connected to it via a second connection 17, together forming an HF circuit. The active electrode 5 is designed, for example, as a cutting loop, and the neutral electrode 6 is advantageously designed as a large-area strip electrode that is applied, for example, to the leg of a patient 7. The arc-measuring device 2 for recording the arc measurements LB+ and LB−, and a further measuring device 3 for recording the current values I and the voltage values U of the HF generator 1, are connected to the connecting leads 16 and 17. The output sides of the measuring devices 2 and 3 are connected to a controlling device 4. Set point values can be supplied to the controlling device 4 via a data memory or via a set point adjuster, which is not shown here (indicated by an arrow 8 in FIG. 1).

Figure 2:
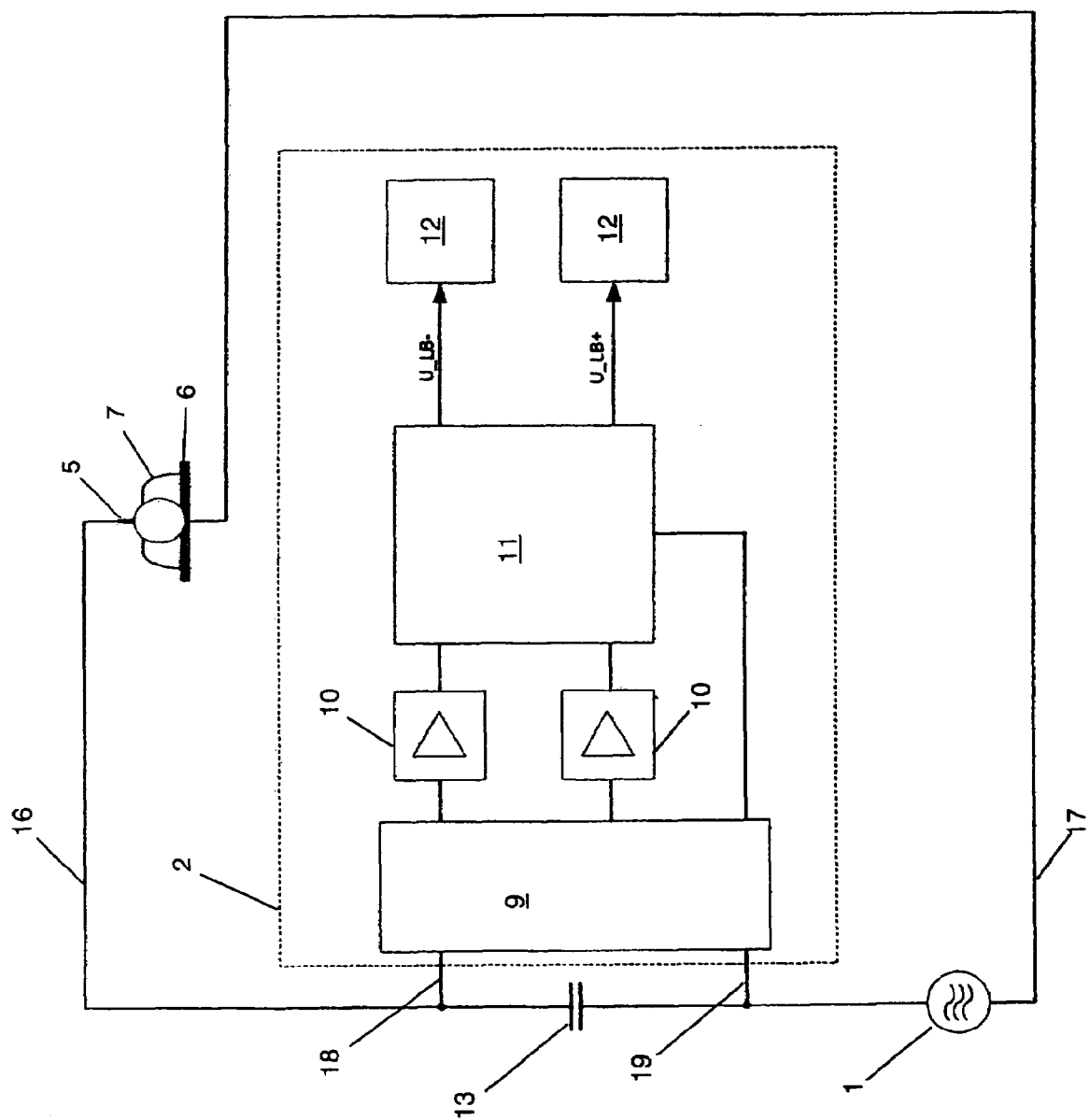
FIG. 2: A schematic circuit diagram of an arc-measuring device.

The schematic circuit diagram of the arc-measuring device 2 is shown in FIG. 2. The measuring device 2 is connected the HF circuit by means of a first connecting lead 18 coupled to the active electrode 5 via a connecting lead 16, and a second connecting lead 19 coupled to the output of the generator 1. An anti-faradization capacitor is inserted in the circuit between connections 18 and 19. The measuring device 2 consists essentially of four functional modules. The first module in the signal chain is the arc-decoupling circuit 9 for separating the positive and negative DC voltage components LB+ and LB− of the HF generator voltage U. Circuit 9 has two outputs for the separated DC voltage signals LB+, LB−, each of which is connected with a signal amplifier 10 (second module). A measurement-processing device 11 (third module), in the form of a microcontroller, is connected to the signal amplifiers 10, and the outputs from the said device in each case lead to a galvanic decoupling circuit 12, for example an optocoupler (fourth module).

Figure 3:
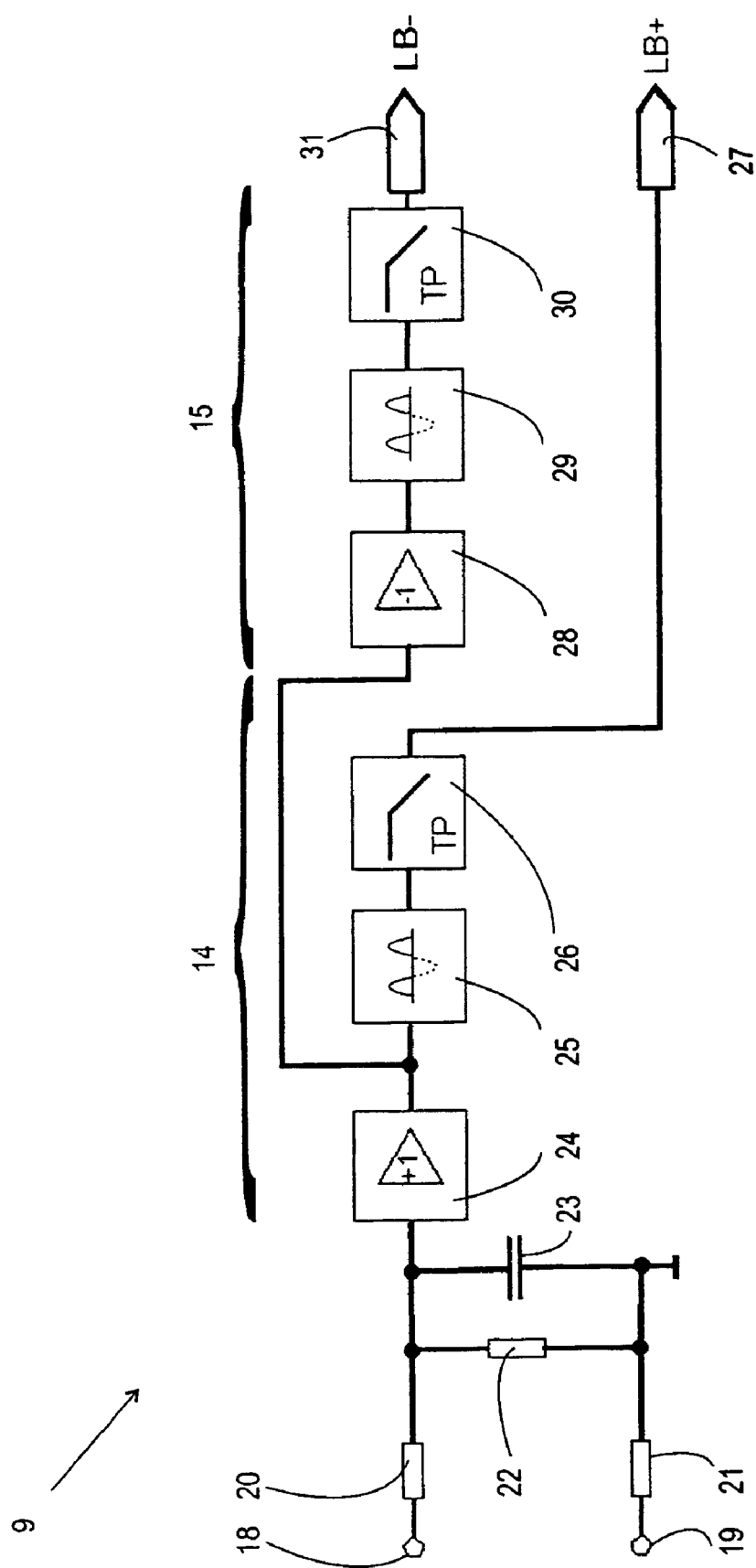
FIG. 3: A functional circuit diagram of an arc-decoupling circuit.
Figure 4:
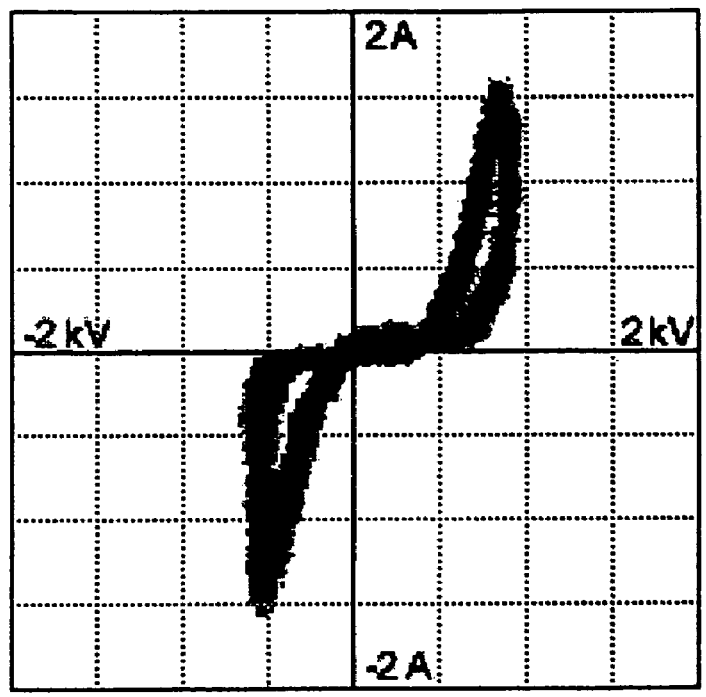
FIG. 4: A current-voltage-hysteresis curve obtained for arc cutting of biological tissue.
Figure 5:
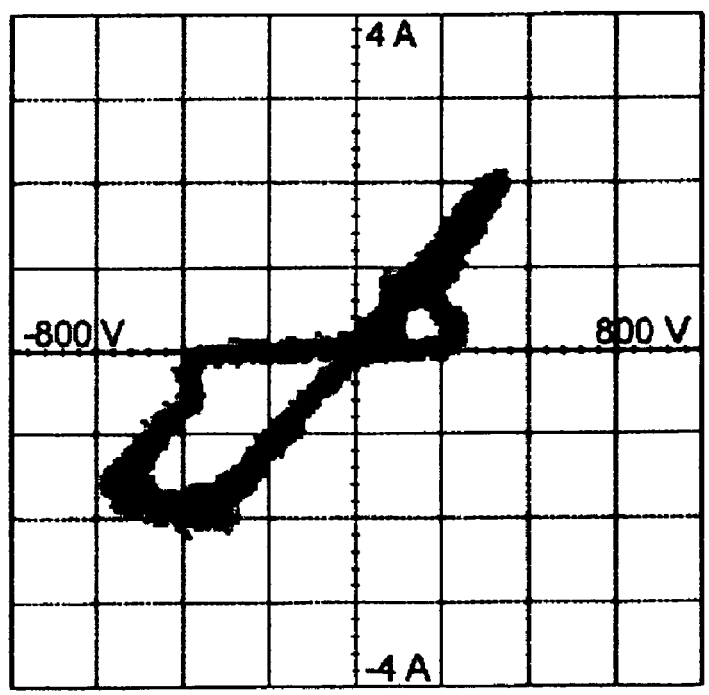
FIG. 5: A current-voltage hysteresis curve obtained during the formation of an electric arc between metal and metal placed on biological tissue.

FIG. 3 shows a functional circuit diagram of the arc-decoupling circuit 9 in detail. The connections 18 and 19 each lead via a resistor circuit 20 or 21, a further, parallel-connected resistor 22, and a parallel capacitor 23, to a first arc sensor sub-circuit 14 of the circuit 9. The connection 18, which for example in the case of monopolar operation can correspond to the active electrode 5 in FIGS. 1 and 2, is connected with the input of a non-inverting amplifier 24. The amplifier 24 acts as a pre-amplifier for the input signal. A rectifying low-pass network, which is shown in FIG. 3 broken down into its functions as a rectifier 25 and a low pass 26, is connected to the output of the amplifier 24 and extracts the DC voltage component from the positive half wave; said DC voltage component can be tapped off as a DC voltage signal LB+ at a signal tap 27. It should be noted that the functional components 25 and 26 of the rectifying low-pass network, which are shown separately in FIG. 1, do not necessarily have to be implemented as separate circuits. Instead, a single circuit that performs both functions can be used. On the other hand, however, it is also possible to assign individual components of the rectifying low-pass network to other elements of the circuit, e.g. to a microprocessor connected to the DC voltage output 27 (LB+).

Furthermore, the output of the amplifier 24 is connected to the input of an inverting amplifier 28 which is part of a second arc sensor sub-circuit 15. The functioning of the sub-circuit 15 is similar to that of the sub-circuit 14. The rectifying low-pass network, which is shown functionally as a rectifier 29 and a low pass 30, extracts the DC voltage component from the negative half-wave; said DC voltage component can be tapped off as a DC voltage signal LB− at a signal tap 31. By reversing the polarity of the input signal of the sub-circuit 15, the rectifying low-pass network of the sub-circuit 15 can be identical in structure to that of the sub-circuit 14, which is advantageous in terms of costs, but is not significant as far as the invention is concerned. It goes without saying that, as regards the variants of the actual implementation, the comments made above in connection with sub-circuit 14 apply analogously.

A method for operating a high-frequency surgical instrument, using a high-frequency generator for cutting and/or coagulating biological tissue with high-frequency current, is based essentially on separately monitoring DC voltage components in the positive and negative half-cycles of a high-frequency AC voltage when an electric arc is formed.

The method according to the invention is explained on the basis of the functioning of the high-frequency surgical device described above.

The current or the arc needed for cutting and/or coagulation is introduced into the tissue of the patient 7 via the active electrode 5 and flows back again to the HF generator 1 via the neutral electrode 6. The arc-decoupling circuit 9 separates the positive and the negative half-waves of the high-frequency AC voltage and separately filters the DC voltage components LB+ and LB−, which occur when the electric arc is formed between the active electrode 5 and the tissue, out of the half-waves. The extracted DC voltage signals LB+, LB− are passed on via the amplifiers 10 to the measurement-processing unit 11, which then processes the signals, using the galvanic decoupling circuits 12, for galvanically separated transmission to the controlling device 4.

From the arc-measuring device 2, the controlling device 4 receives the currently processed DC voltage signals LB+ and LB−, and from the measuring device 3 it receives the currently effective values of the voltage U and the current I of the HF generator 1, compares them with the set points for these values as set or stored in the set point adjuster 8, and adjusts a desired voltage $U_{Soll}$ for an arc that is optimal for the application. If, on the basis of a non-allowed value for a DC voltage component, the controlling device 4 detects that the high-frequency surgical apparatus is operating irregularly, a warning signal is emitted or a control signal is generated to lower/shut off the high frequency AC voltage or the HF current via the power switching unit.

Naturally, the embodiments described in the specific description and in the Figures are merely illustrative exemplary embodiments of the invention. A person skilled in the art is provided with a broad range of possible variations. In particular, the invention can be used both for monopolar as well as for bipolar or multipolar applications.

LIST OF REFERENCE NUMBERS

1 HF generator
2 Arc-measuring device
3 Measuring device
4 Controlling device
5 Active electrode
6 Neutral electrode
7 Patient
8 Set point adjuster
9 Arc-decoupling circuit
10 Amplifier
11 Measurement-processing device
12 Galvanic decoupling circuit
13 Anti-faradization capacitor
14 Arc sensor sub-circuit
15 Arc sensor sub-circuit
16 Connecting lead
17 Connecting lead
18 Connection
19 Connection
20 Resistor
21 Resistor
22 Resistor
23 Capacitor
24 Non-inverting amplifier
25 Rectifier
26 Low pass
27 Signal tap
28 Inverting amplifier
29 Rectifier
30 Low pass
31 Signal tap

The invention claimed is:

1. A high-frequency surgical apparatus in which, for the purpose of cutting and/or coagulating biological tissue by means of high-frequency current, a high-frequency generator having a first electrode and a second electrode forms a high-frequency circuit through the tissue being treated, with an electric arc being formed, said apparatus having a measuring device to detect DC voltage components forming in the high frequency circuit when the arc is formed, said DC voltage components being usable for controlling the high-frequency generator via a controlling device, wherein the measuring device (2) has an arc-decoupling circuit (9) which separates the DC voltage components in the positive half-wave of the high-frequency AC voltage from the DC voltage components in the negative half-wave of the high-frequency AC voltage and makes available at least one of the separated DC voltage components as a signal for subsequent processing in the controlling device (4).

2. A high-frequency surgical apparatus according to claim 1, wherein the decoupling circuit (9) makes the DC voltage components from the positive as well as from the negative half wave of the high-frequency AC voltage available as signals for subsequent processing in the controlling device (4).

3. A high-frequency surgical apparatus according to claim 1, wherein a measurement-processing device (11) is provided downstream from the arc-decoupling circuit (9), in which the separated DC voltage components or values derived therefrom can be processed for galvanically separated signal transmission to the subsequent controlling device (4).

4. A high-frequency surgical apparatus according to claim 1, wherein the controlling device (4) is associated with a computer unit having a processing algorithm and a data memory or a set point adjuster (8) in which at least one set point value for at least one separated DC voltage component or a value derived therefrom can either be stored or adjusted.

5. A high-frequency surgical apparatus according to claim 1, wherein the controlling device (4) has means for generating a control signal for controlling at least one of the parameters influencing the power output, taking into account the evaluation of at least one of the separated DC voltage components.

6. A high-frequency surgical apparatus according to claim 1, wherein the controlling device (4) is provided with means for putting out a warning signal based on the evaluation of at least one of the separated DC voltage components.

7. A high-frequency surgical apparatus according to claim 6, wherein the means for emitting the warning signal takes the form of a monitor having an optical and/or acoustic display.

8. A method for operating a high-frequency surgical apparatus in which, for the purpose of cutting and/or coagulating biological tissue using high frequency current, a high-frequency generator having a first electrode and a second electrode creates a high frequency circuit through the tissue undergoing treatment, with an electric arc being formed, and in which DC voltage components generated in the high frequency circuit when the electric arc is formed are used to control the high-frequency generator, said method comprising: separately measuring at least one of the positive and negative half-waves of the high-frequency AC voltage of the high-frequency circuit to determine any occurrence of DC voltage components, and generating an appropriate signal in the event of a DC voltage component deviating from a set point value.

9. A method according to claim 8, wherein the positive as well as the negative half-waves of the high-frequency AC voltage of the high-frequency circuit are separately measured to determine any occurrence of DC voltage components, and further wherein in the event of a DC voltage component deviating from a set point value, an appropriate signal is generated.

10. A method according to claim 8, wherein in the event of at least one DC voltage component deviating from the set point value in the half-wave of the high-frequency AC voltage (U), an acoustic and/or optical warning signal is generated.

11. A method according to claim 8, wherein in the event of at least one DC voltage component deviating from the associated set point value in the half-wave of the high-frequency AC voltage (U), a control signal is generated through which the high-frequency AC voltage (U) is reduced or switched off.

12. A high-frequency surgical apparatus in which, for the purpose of cutting and/or coagulating biological tissue by means of high-frequency current, a high-frequency generator having a first electrode and a second electrode forms a high-frequency circuit through the tissue being treated, with an electric arc being formed, said apparatus having a measuring device to detect DC voltage components forming in the high frequency circuit when the arc is formed, said DC voltage components being usable for controlling the high-frequency generator via a controlling device, wherein the measuring device (2) has an arc-decoupling circuit (9) which separates the DC voltage components in the positive half-wave of the high-frequency AC voltage from the DC voltage components in the negative half-wave of the high-frequency AC voltage and provides at least one of the separated DC voltage components as a signal to a controlling device (4), the controlling device (4) compares the signal from the measuring device (2) with a set point value, and in the case of the signal deviating from the set point value, generates an appropriate signal and/or reduces or switches off the high-frequency AC voltage (U).

\* \* \* \* \*